(12) United States Patent
Senda et al.

(10) Patent No.: US 8,173,403 B2
(45) Date of Patent: May 8, 2012

(54) PROCESS FOR PRODUCING USEFUL SUBSTANCE USING IMMOBILIZED ENZYME

(75) Inventors: Yoshitaka Senda, Kamisu (JP); Jun Saito, Kamisu (JP); Keigo Hanaki, Kamisu (JP); Toshiteru Komatsu, Kamisu (JP)

(73) Assignee: Kao Corporation, Tokyo (JP)

( * ) Notice: Subject to any disclaimer, the term of this patent is extended or adjusted under 35 U.S.C. 154(b) by 170 days.

(21) Appl. No.: 12/517,574

(22) PCT Filed: Dec. 14, 2007

(86) PCT No.: PCT/JP2007/001401
§ 371 (c)(1),
(2), (4) Date: Jun. 4, 2009

(87) PCT Pub. No.: WO2008/072381
PCT Pub. Date: Jun. 19, 2008

(65) Prior Publication Data
US 2010/0047883 A1  Feb. 25, 2010

(30) Foreign Application Priority Data
Dec. 15, 2006  (JP) .................................. 2006-337890

(51) Int. Cl.
*C12P 7/64* (2006.01)
*C12N 11/00* (2006.01)
*C12N 11/14* (2006.01)

(52) U.S. Cl. .......................... 435/134; 435/174; 435/176

(58) Field of Classification Search .................. 435/109, 435/44, 137, 41, 176, 134, 147, 289
See application file for complete search history.

(56) References Cited

U.S. PATENT DOCUMENTS

| | | | |
|---|---|---|---|
| 4,629,742 A * | 12/1986 | Brady et al. | 521/55 |
| 5,010,004 A | 4/1991 | Kosugi et al. | |
| 5,292,649 A * | 3/1994 | Kosugi et al. | 435/136 |
| 6,218,138 B1 * | 4/2001 | Ilhan et al. | 435/45 |
| 6,258,575 B1 * | 7/2001 | Shimizu et al. | 435/134 |
| 7,517,674 B2 * | 4/2009 | Komatsu et al. | 435/134 |
| 2003/0013165 A1 | 1/2003 | Komatsu et al. | |
| 2005/0277180 A1 * | 12/2005 | Komatsu et al. | 435/134 |
| 2006/0292675 A1 | 12/2006 | Saito et al. | |
| 2009/0298142 A1 * | 12/2009 | Saito et al. | 435/134 |

FOREIGN PATENT DOCUMENTS

| | | |
|---|---|---|
| EP | 1 736 549 | 12/2006 |
| JP | 61-85195 A | 4/1986 |
| JP | 1-98494 | 4/1989 |
| JP | 2000 160188 | 6/2000 |
| JP | 2000-160188 A | 6/2000 |
| JP | 2000 297295 | 10/2000 |

OTHER PUBLICATIONS

Wisdom, R. A. et al., "Enzymatic Interesterification of Fats: Laboratory and Pilot-Scale Studies with Immobilized Lipase from *Rhizopus arrhizus*", Biotechnology and Bioengineering, vol. 29, No. 9, pp. 1081-1085, (1987).
H-Kittikun, A. et al., "Continuous Production of Fatty Acids from Palm Olein by Immobilized Lipase in a Two-Phase System."JAOCS, vol. 77, No. 6, pp. 599-603, (2000).
U.S. Appl. No. 12/518,285, filed Jun. 9, 2009, Saito, et al.
U.S. Appl. No. 12/067,664, filed Mar. 21, 2008, Saito, et al.
Extended Search Report issued Mar. 1, 2012 in European application No. 07849831.8-1521.
Watanabe et al, Process Biochemistry, (2005) vol. 40. pp. 637-643.

\* cited by examiner

*Primary Examiner* — Chris R Tate
*Assistant Examiner* — Douglas F White
(74) *Attorney, Agent, or Firm* — Oblon, Spivak, McClelland, Maier & Neustadt, L.L.P.

(57) ABSTRACT

The present invention relates to a process for producing a useful substance, the process includes feeding a liquid mixture formed of two liquid phases into a fixed bed-type reaction column packed with an immobilized enzyme, and allowing the liquid mixture to flow in the same direction in a co-current manner to perform a reaction. The packing thickness of the immobilized enzyme per stage of the fixed bed-type reaction column having an equivalent circular diameter of 35 mmφ or larger is 10 to 200 mm. The flow of the reaction liquid inside the column can be made uniform, and as a result, reactivity and productivity is enhanced.

6 Claims, No Drawings

PROCESS FOR PRODUCING USEFUL SUBSTANCE USING IMMOBILIZED ENZYME

FIELD OF THE INVENTION

The present invention relates to a process for producing a useful substance through a reaction using a fixed bed-type reaction column packed with an immobilized enzyme.

BACKGROUND OF THE INVENTION

As the reaction which is carried out by passing a liquid through a fixed bed-type reaction column, there are known reactions utilizing an immobilized enzyme, which are used in the production of L-aspartic acid, production of transesterified oils and fats, hydrolysis of lactose, hydrolysis of oils and fats, and the like. These reactions are normally carried out by use of the simplest drum type reactors, because their heating values are relatively small.

Among the reactions utilizing an immobilized enzyme, in the case of allowing two or more kinds of liquids to flow through the reaction column as in the case of the hydrolysis of oils and fats, it is preferable to pass the reaction liquids in a uniformly mixed state, from the viewpoint of enhancing the reaction efficiency. In this case, the oil phase substrate and the aqueous phase substrate used in the hydrolysis do not form into a single phase even if mixed, so it is common for this mixture to become an emulsion. On the other hand, it is difficult for emulsion particles to reach the enzyme which is adsorbed to the interior of pores of the support, so there has been a technology which allows the rate of liquid passage not to exceed an extent to which the reaction liquids are not emulsified (see Patent Document 1).

Furthermore, as the process of allowing an oil phase substrate and an aqueous phase substrate to flow through a fixed bed, there may be mentioned processes of allowing the substrates to flow in a countercurrent manner (see Patent Documents 1 and 2), and processes of allowing the substrates to flow in a co-current manner (see Patent Document 3). However, the former processes require special structures and operating processes, so it is common to make use of a method allowing the substrates to flow in a co-current manner.

[Patent Document 1] JP-A-61-85195
[Patent Document 2] JP-A-01-98494
[Patent Document 3] JP-A-2000-160188

DISCLOSURE OF THE INVENTION

A purpose of the present invention is to provide a process for producing a useful substance, which includes feeding a liquid mixture formed of two liquid phases into a fixed bed-type reaction column packed with an immobilized enzyme, and allowing the liquid mixture to flow in the same direction in a co-current manner to perform a reaction, wherein the packing thickness of the immobilized enzyme per stage of the fixed bed-type reaction column having an equivalent circular diameter of 35 mmφ or larger is 10 to 200 mm.

An other purpose of the present invention is to provide a process for producing a useful substance, which includes feeding a liquid mixture formed of two liquid phases into a fixed bed-type reaction column packed with an immobilized enzyme, and allowing the liquid mixture to flow in the same direction in a co-current manner to perform a reaction, wherein a multistage fixed bed-type reaction column is used in which a packing unit that is packed with the immobilized enzyme such that the packing thickness per stage of the fixed bed-type reaction column having an equivalent circular diameter of 35 mmφ or larger is 10 to 200 mm, is stacked in at least two or more stages, wherein each packing unit is spaced apart at a distance of at least equal to or less than the thickness of the packing unit.

An other purpose of the present invention is to provide a fixed bed-type reaction column having an equivalent circular diameter of 35 mmφ or larger, and a packing thickness of the immobilized enzyme per stage is 10 to 200 mm.

PREFERRED EMBODIMENTS OF THE INVENTION

In the processes performing a reaction by allowing a liquid mixture formed of two liquid phases, to flow through a fixed bed-type reaction column packed with an immobilized enzyme, it was found that there was a problem in which as the diameter of the reaction column is increased, the flow of the reaction liquid in the column becomes non-uniform, and there occur parts where the reaction does not efficiently proceed, as a result the reactivity being decreased. In this case, if it is simply attempted to lengthen the time of contact between the immobilized enzyme and the reaction liquid in order to increase the reactivity, there is also a problem in which productivity (flow rate) decreases.

Therefore, the present invention relates to a process for producing a useful substance by allowing a liquid mixture formed of two liquid phases, to flow through a fixed bed-type reaction column packed with an immobilized enzyme to perform a reaction, in which the useful substance is more efficiently produced by increasing reactivity without decreasing the flow rate, and thereby enhancing productivity.

Thus, the inventors of the present invention analyzed the characteristics of the passage of the reaction liquid in a fixed bed-type reaction column packed with an immobilized enzyme, and as a result, they found that when the diameter of the fixed bed-type reaction column is increased, there occurs non-uniformization of the reaction liquid in the column from a site where the packing thickness exceeds a certain value, due to the difference in the flow condition between the oil phase and the aqueous phase, and the reactivity decreases. There, the inventors found that when the packing thickness of the immobilized enzyme per stage of the fixed bed-type reaction column is defined, and the liquid-liquid biphasic flow is rectified, productivity can be enhanced while high reactivity is maintained.

According to the present invention, in the process for producing a useful substance by feeding a liquid mixture formed of two liquid phases into a fixed bed-type reaction column packed with an immobilized enzyme, the flow of the reaction liquid in the column can be made uniform, and as a result, reactivity and productivity can be enhanced. Particularly, in regard to the hydrolysis of oils and fats, fatty acids can be efficiently produced by allowing the enzymatic activity to effectively appear.

In the present invention, a liquid mixture (reaction liquid) formed of two liquid phases is fed into a fixed bed-type reaction column packed with an immobilized enzyme. The fixed bed-type reaction column (herein after, also referred to as "enzyme column") is meant by that an immobilized enzyme is packed in a column or the like, so that the reaction liquid can flow through the gaps between supports of immobilized enzyme, and the pores of the support. The fixed bed-type reaction column may be constituted of one fixed bed-type reactor having one stage of a packing unit packed with an immobilized enzyme, or may also be a multistage fixed bed-type reaction column having two or more stages of the packing units stacked so that each packing unit is spaced apart.

The term two liquid phases means the state in which two types of liquids do not form a single phase even after mixing, and includes the state being phase separated or a uniform state as well as an emulsified state.

According to an aspect of the present invention, the process is preferably a process for producing fatty acids as the useful substance by a hydrolysis reaction of oils and fats, in which an oil and fat hydrolysis enzyme adsorbed onto a support is used as the immobilized enzyme, and as the two liquid phases, an oil phase substrate and an aqueous phase substrate are allowed to flow through an enzyme column packed with the oil and fat hydrolysis enzyme.

In the present invention, the two liquid phases are allowed to flow in the same direction in a co-current manner. In this case, the two liquid phases may be mixed in advance and supplied in an emulsified state, or may also be supplied in the form of separated phases. Furthermore, the two liquid phases may also be supplied alternately at an interval of a predetermined time period. The supply of the respective substrates into the enzyme column may be carried out in a downward flow from the top of the column to the bottom of the column, or may also be carried out in an upward flow from the bottom of the column to the top of the column.

The immobilized enzyme used in the present invention is an enzyme supported by adsorption or the like. As for the support, there may be mentioned inorganic supports such as celite, diatomaceous earth, kaolinite, silica gel, molecular sieves, porous glass, activated carbon, calcium carbonate, and ceramics; organic polymers such as ceramic powders, polyvinyl alcohol, polypropylene, chitosan, ion exchange resins, hydrophobic adsorption resins, chelating resins and synthetic adsorption resins; and the like. Particularly from the viewpoint of having high water retaining power, ion exchange resins are preferred. Furthermore, among the ion exchange resins, porous resins are preferred from the viewpoint that the large surface area of the porous resins can increase the amount of adsorption of the enzyme.

The particle size of the resin used as the support is preferably 100 to 1000 µm, and more preferably 250 to 750 µm. The pore size is preferably 10 to 150 nm, and more preferably 10 to 100 nm. As for the material, phenol formaldehyde-based, polystyrene-based, acrylamide-based, divinylbenzene-based resins and the like may be mentioned, and in particular, phenol formaldehyde-based resins (for example, Duolite A-568 manufactured by Rohm and Haas Company) are preferred from the viewpoint of enhancing the enzyme adsorptivity.

The enzyme used for the immobilized enzyme of the present invention is not particularly limited, but from the viewpoint of having a large effect of enhancing productivity, lipases as the enzymes for hydrolyzing oils and fats are preferred. The lipases that can be used may be animal-derived and plant-derived lipases, as well as commercially available, microorganism-derived lipases. As for the microorganism-derived lipases, there may be mentioned those originating from genus *Rhizopus*, genus *Aspergillus*, genus *Mucor*, genus *Pseudomonas*, genus *Geotrichum*, genus *Penicillium*, genus *Candida*, and the like.

The temperature for carrying out immobilization of an enzyme can be determined based on the properties of the enzyme, but is preferably 0 to 60° C., and particularly preferably 5 to 40° C., where deactivation of an enzyme does not occur. Furthermore, the pH of the enzyme solution used at the time of immobilization may be within a range where deactivation of the enzyme does not occur, and can be determined based on the properties of the enzyme as in the case of temperature, but is preferably pH 3 to 9. In order to maintain this pH, a buffer solution is used, and examples of the buffer solution include acetate buffer solution, phosphate buffer solution, Tris-hydrochloric acid buffer solution, and the like. The enzyme concentration in the enzyme solution is preferably a concentration which is equal to or less than the saturation solubility of the enzyme, while being sufficient, from the viewpoint of immobilization efficiency. As for the enzyme solution, a supernatant obtained after removing the insoluble part by centrifugation as necessary, or a solution purified by ultrafiltration or the like, can also be used. The mass of enzyme used may vary depending on the activity of that enzyme, but is preferably 5 to 1000% by mass, and more preferably 10 to 500% by mass, based on the mass of support.

In the case of immobilizing an enzyme, the support and the enzyme may be directly adsorbed, but in order to obtain an adsorption state which is likely to show high activity, it is preferable to treat the support in advance with a fat-soluble fatty acid or a derivative thereof, before adsorbing the enzyme. As for the method of contacting a fat-soluble fatty acid or a derivative thereof with the support, these materials may be directly added into water or an organic solvent; however, to make the dispersibility good, the fat-soluble fatty acid or the derivative thereof may be first dispersed and dissolved in an organic solvent, and then the solution may be added to the support which has been dispersed in water. As for this organic solvent, chloroform, hexane, ethanol and the like may be mentioned. The mass of use of the fat-soluble fatty acid or a derivative thereof is preferably 1 to 500% by mass, and particularly preferably 10 to 200% by mass, based on the mass of support. The contacting temperature is preferably 0 to 100° C., and more preferably 20 to 60° C., and the contacting time is preferably about 5 minutes to 5 hours. The support which has undergone this treatment is filtered and recovered, but may also be dried. The drying temperature is preferably room temperature to 100° C., and drying under reduced pressure may also be performed.

Among the fat-soluble fatty acids or derivatives thereof for treating the support in advance, there may be mentioned, as for the fat-soluble fatty acids, saturated or unsaturated, linear or branched fatty acids having 4 to 24 carbon atoms, and preferably 8 to 18 carbon atoms, which may have a hydroxyl group. Specific examples thereof include capric acid, lauric acid, myristic acid, oleic acid, linolic acid, α-linolenic acid, ricinolic acid, isostearic acid and the like. Furthermore, as the derivatives of the fat-soluble fatty acids, there may be mentioned esters of these fat-soluble fatty acids and monohydric or polyhydric alcohols or sugars, phospholipids, products obtained by adding ethylene oxide to these esters, and the like. Specific examples thereof include methyl esters, ethyl esters, monoglycerides and diglycerides of the aforementioned fatty acids, ethylene oxide adducts thereof, polyglycerin esters, sorbitan esters, sucrose esters thereof, and the like. It is preferable that these fat-soluble fatty acids and derivatives thereof are all in the liquid state at normal temperature, in view of the process of immobilizing an enzyme on a support. These fat-soluble fatty acids or derivatives thereof may be used in combination of two or more species, and naturally occurring fatty acids such as rapeseed fatty acids and soybean fatty acids can also be used.

The hydrolytic activity of the immobilized enzyme is preferably 20 U/g or greater, more preferably 100 to 10000 U/g, and even more preferably in the range of 500 to 5000 U/g. Here, 1 U of the enzyme indicates the capacity of the enzyme which produces 1 µmol of free fatty acids in one minute when a mixed liquid of oils and fats:water=100:25 (mass ratio) is subjected to hydrolysis for 30 minutes at 40° C., while stirring and mixing the mixed liquid. The hydrolytic activity of the immobilized enzyme (U/g-oil) imparted per unit mass of the oils and fats, and the time taken to reach a certain rate of hydrolysis are in an approximately inversely proportional relationship.

In the case of performing hydrolysis by using a packed bed (enzyme column) packed with an immobilized enzyme, the rate of degradation may vary with the conditions for liquid supply (rate of liquid passage, temperature, and the like), but from the rate of hydrolysis of the oils and fats at the outlet of the enzyme packed bed, the time taken by hydrolysis (retention time in the packed bed), the mass of oils and fats present in the packed bed (g-oil), and the packing mass of the immobilized enzyme (g), the apparent activity (U/g) of the immobilized enzyme is determined. In addition, in order to determine the mass of oils and fats present in the packed bed, the mass is determined by multiplying the volume of the immobilized enzyme packing unit, with the porosity of the packing unit, the volume ratio of the oils and fats in the reaction liquid, and the specific gravity of the oils and fats.

It is preferable that one component of the liquid mixture which forms two liquid phases, as used in the present invention, be an oil phase substrate. The oil phase substrate refers mainly to plant oils, animal oils, or oils and fats combining these, but the oils and fats may also contain triacylglycerols, as well as diacylglycerols, monoacylglycerols or fatty acids, or may also contain fatty acids obtain able as a result of hydrolysis. Specific examples of the oil phase substrate include plant oils such as rapeseed oil, soybean oil, sunflower oil, palm oil and linseed oil; animal oils such as beef tallow, pork fats and fish oil; and the like, or oils and fats in combination of these. In regard to these oils and fats, deodorized oil, as well as undeodorized oils and fats which have not been deodorized in advance can be used, but it is preferable to use undeodorized oil and fat for part or all of these oils and fats, from the viewpoint of reducing trans unsaturated fatty acids and conjugated unsaturated fatty acids, so as to allow plant sterols, plant sterol fatty acid esters, and tocopherols derived from the raw material oils and fats to remain. In the oil phase substrate, oil-soluble components such as fatty acids other than the aforementioned oils and fats may also be mixed in. The fatty acids also refer to those containing one or more of the aforementioned glycerides, in addition to the fatty acids obtain able as a result of hydrolysis.

It is preferable that the other component of the liquid mixture which forms two liquid phases, as used in the present invention, be an aqueous phase substrate. The aqueous phase substrate is water, but the substrate may also have other water-soluble components mixed therein, such as glycerin which is obtain able as a result of hydrolysis.

In the present invention, an enzyme column having an equivalent circular diameter of 35 mmφ or larger and a packing thickness of the immobilized enzyme per stage of 10 to 200 mm is used to perform the reaction. As the equivalent circular diameter of the enzyme column is increased to be larger than 35 mmφ, there is a tendency that the flow of the reaction liquid becomes non-uniform, and reactivity is decreased.

The equivalent circular diameter of the enzyme column is preferably set at 35 to 10,000 mmφ, more preferably 35 to 7,500 mmφ, and even more preferably 35 to 5,000 mmφ, from the viewpoints of reactivity and productivity.

Here, the equivalent circular diameter means, in the case where the enzyme column is circular in shape, the diameter of the column, and in the case where the enzyme column is polygonal in shape, the diameter of a circle having the same area as the projected area, which is determined by the following formula (1), with A being the projected area:

$$D=2(A/\pi)^{0.5} \quad (1)$$

(D: equivalent circular diameter (mm), A: projected area of polygon (mm$^2$))

The shape of the enzyme column used in the present invention is preferable if the shape can withstand the pressing force of the pump used. Furthermore, it is preferable that a jacket is provided around the enzyme column so as to adjust the reaction liquid flowing through inside the enzyme column to a temperature appropriate for the enzyme reaction.

The temperature in the enzyme column is preferably set at 0 to 60° C., and more preferably 20 to 40° C., to induce the activity of the immobilized enzyme more effectively. The length of the enzyme column may be any length necessary for obtaining a desired degradation rate, but from the viewpoints of reactivity, loss of the pressure inside the column, and the like, the length is in the range of 0.01 to 10 m, and preferably 0.1 to 5 m.

According to the present invention, the immobilized enzyme is packed in the enzyme column to a thickness of 10 to 200 mm per stage. As such, by defining the packing thickness of the immobilized enzyme, the flow of the reaction liquid becoming non-uniform can be prevented, and since the flow of the reaction liquid is rectified, the enzymatic activity is effectively appeared, and hydrolysis can be efficiently carried out. The packing thickness of the immobilized enzyme per stage of the enzyme column is preferably 10 to 200 mm from the viewpoint of reactivity, and is more preferably 15 to 200 mm, and even more preferably 75 to 200 mm.

Furthermore, in the case of using a multistage fixed bed-type reaction column, each packing unit is spaced apart, preferably at a distance of at least equal to or less than the thickness of the packing unit of the immobilized enzyme from the viewpoints of reactivity, production and the like, and is preferably 1 to 200 mm, more preferably 5 to 200 mm, and even more preferably 15 to 200 mm. When this multistage fixed bed-type reaction column is used, higher reactivity can be maintained even without mixing in order.

The packing unit is preferably stacked in 2 to 30 stages, and more preferably stacked in 3 to 20 stages, with each packing unit being spaced apart, from the viewpoints of reactivity, production, or the like.

As for the method of supplying the reaction liquid to the enzyme column, the substrates may be respectively and separately supplied through pipes which are directly connected to the enzyme column, or the supply may also be carried out through a shared pipe, but in view of operability, it is preferable to carry out the supply separately through pipes directly connected to the enzyme column.

The linear velocity of liquid passage of the reaction liquid in the enzyme column is preferably 1 to 400 mm/min, and more preferably 5 to 200 mm/min. This linear velocity of liquid passage (mm/min) means a value expressed as a quotient of the amount of liquid transfer per minute (mm$^3$/min) (or also referred to as the velocity of liquid transfer ($10^{-3}$ mL/min)), divided by the cross-sectional area of the packed bed (mm$^2$). As the pressure inside the packed column increases as a result of increasing the linear velocity of liquid passage, liquid passage becomes difficult, and an enzyme packed column having high pressure resistance is required, and also, there may occur situations in which the immobilized enzyme is crushed due to the increase in the pressure inside the column. Therefore, it is preferable to set the linear velocity of liquid passage at 400 mm/min or less. Furthermore, it is preferable to set the linear velocity of liquid passage at 1 mm/min or greater, from the viewpoint of productivity. Since the activity of the immobilized enzyme changes with the linear velocity of liquid passage, a reaction appropriate for the desired production capacity and manufacturing costs can be carried out by selecting the optimum linear velocity of liquid passage and thereby determining the reaction conditions.

The retention time of the reaction liquid in the immobilized enzyme packing unit inside the enzyme column is preferably 30 seconds to 60 minutes, and more preferably 1 minute to 40 minutes, in view of avoiding the equilibrium state of the hydrolysis reaction, and more effectively eliciting the activity of the immobilized enzyme, to thereby enhance the productivity. The retention time is expressed as the value obtained by multiplying the thickness of the packed bed (mm) with the porosity, and dividing the product with the linear velocity of liquid passage (mm/min).

In the present invention, from the viewpoint of good balance between reactivity, productivity and the like, the reaction liquid which passed through the enzyme column may be directly used as the completed reaction product. Alternatively, the process may be carried out such that the reaction liquid is first subjected to oil-water separation, freshwater is added after the oil phase is subjected to fractionation, and the mixture is supplied again into the same enzyme column by the same method as described above, and the reaction liquid may be repeatedly passed until the desired reaction ratio is obtained. Furthermore, the process may also be carried out such that the reaction liquid is first subjected to oil-water separation, the oil phase is subjected to fractionation, fresh water is added, and the mixture is supplied again into another enzyme column by the same method as described above, to thus perform a continuous reaction. The process may also be carried out by a pseudo-countercurrent method in which an oil phase having a higher rate of degradation is reacted with a fresh aqueous phase, by using a plurality of enzyme columns, and while performing oil-water separation of the reaction liquid, supplying the oil phase into the subsequent enzyme column and supplying the aqueous phase into the previous enzyme column. As for the oil-water separation method for the reaction liquid, oil-water separators of spontaneously settling type, centrifuging type and the like are generally used, but are not particularly limited.

EXAMPLES

Conditioning of Immobilized Lipase

One part by mass of Duolite A-568 (manufactured by Rohm and Haas Company, particle size distribution 100 to 1000 μm) was stirred for one hour in 10 parts by mass of $\frac{1}{10}$N NaOH solution. After filtering, the mixture was washed with 10 parts by mass of ion exchanged water, and pH equilibration was carried out with 10 parts by mass of 500 mM phosphate buffer solution (pH 7). Thereafter, pH equilibration was carried out twice for two hours each, with 10 parts by mass of 50 mM phosphate buffer solution (pH 7). Subsequently, filtration was performed to recover the support, and then ethanol substitution was performed for 30 minutes with 5 parts by mass of ethanol. After filtering the resultant, 5 parts by mass of ethanol containing 1 part by mass of ricinolic acid was added, and ricinolic acid was adsorbed onto the support for 30 minutes. After recovering the support by filtration, the support was washed for four times for 30 minutes each, with 5 parts by mass of 50 mM phosphate buffer solution (pH 7), ethanol was removed, and the support was recovered by filtration. Subsequently, the support was contacted for 5 hours with an enzyme solution in which 1 part by mass of a commercially available lipase (Lipase AY, Amano Pharmaceutical Co., Ltd.) was dissolved in 9 parts by mass of 50 mM phosphate buffer solution (pH 7), to perform immobilization. The resultant was filtered, and the immobilized enzyme was recovered and washed with 10 parts by mass of 50 mM phosphate buffer solution (pH 7), to remove any unimmobilized enzymes or proteins. Subsequently, 4 parts by mass of rapeseed oil which actually performs degradation was added, and the mixture was stirred for 12 hours. The above-described operation was all performed at 20° C. Thereafter, the immobilized enzyme was separated from the oil and fat by filtration, and was used as the immobilized enzyme. As a result, there was obtained an immobilized lipase which exhibited a hydrolytic activity of 2700 U/g (dry mass). The average mass-based particle size of the immobilized enzyme was 311 μm.

Reference Example 1

A column made of stainless steel (inner diameter 10 mm, height 1400 mm) attached with a jacket was packed with 27.0 g (dry mass) of the aforementioned immobilized lipase (packing height 1200 mm), and the column was maintained at 35° C. with the jacket. A liquid prepared by mixing rapeseed oil and distilled water at a mass ratio of 10:6 was supplied from the top of the column at a rate of 1.57 mL/min, and a hydrolysis reaction was performed. The results are presented in Table 1.

Reference Example 2

A hydrolysis reaction was performed in the same procedure as in Reference Example 1, except that a packing unit (packing height 200 mm) having 4.83 g on a dry basis of the aforementioned immobilized lipase packed in a column made of stainless steel (inner diameter 10 mm, height 1950 mm) equipped with a jacket was stacked in 6 stages, with each packing unit being spaced apart (height 150 mm). The results are presented in Table 1.

As shown in Table 1, it became clear that in the case where the diameter of the enzyme column was about 10 mmϕ, the (apparent) activity of the immobilized enzyme was effectively appeared, irrespective of the packing height of the immobilized enzyme.

Example 1

A column made of stainless steel (inner diameter 70 mm, height 150 mm) attached with a jacket was packed with 0.16 kg (dry mass) of the aforementioned immobilized lipase (packing height 150 mm), and the column was maintained at 35° C. with the jacket. A liquid prepared by mixing rapeseed oil and distilled water at a mass ratio of 10:6 was supplied from the top of the column at a rate of 77 mL/min, and a hydrolysis reaction was performed. The results are presented in Table 1. In addition, the rate of degradation in the table was calculated by dividing the acid value determined by analysis, by the saponification value. The acid value was measured by the method described in American Oil Chemists. Society Official Method Ca 5a-40, and the saponification value was measured by the method described in American Oil Chemists. Society Official Method Cd 3a-94.

Example 2

A hydrolysis reaction was performed in the same procedure as in Example 1, except that 0.17825 kg on a dry basis of the aforementioned immobilized lipase was packed (packing height 150 mm) in a column made of stainless steel (inner diameter 70 mm, height 150 mm) equipped with a jacket. Subsequently, the reaction liquid which had passed through the column was first subjected to oil-water separation to fractionate the oil phase, subsequently fresh water was added and mixed, and the mixture was supplied again into another column having the same shape. The hydrolysis reaction was performed four times in total by the same procedure. The results are presented in Table 1.

Example 3

A hydrolysis reaction was performed in the same procedure as in Example 1, except that 0.21 kg on a dry basis of the aforementioned immobilized lipase was packed (packing height 170 mm) in a column made of stainless steel (inner diameter 76.4 mm, height 250 mm) equipped with a jacket, and the rate of liquid supply was set at 92 mL/min. Subsequently, the reaction liquid which had passed through the column was first subjected to oil-water separation to fractionate the oil phase, subsequently fresh water was added and mixed, and the mixture was supplied again into another column having the same shape. The hydrolysis reaction was performed eight times in total by the same procedure. The results are presented in Table 1.

Example 4

A hydrolysis reaction was performed in the same procedure as in Example 1, except that a packing unit (packing height 150 mm) having 0.178 kg on a dry basis of the aforementioned immobilized lipase packed in a column made of stainless steel (inner diameter 70 mm, height 1050 mm) equipped with a jacket was stacked in four stages, with each packing unit being spaced apart (height 150 mm). The results are presented in Table 1.

Example 5

A hydrolysis reaction was performed in the same procedure as in Example 1, except that 13.37 kg on a dry basis of the aforementioned immobilized lipase was packed (packing height 150 mm) in a column made of stainless steel (inner diameter 600 mm, height 150 mm) equipped with a jacket, and the rate of liquid supply was set at 5655 mL/min. The results are presented in Table 2.

Example 6

A hydrolysis reaction was performed in the same procedure as in Example 1, except that a packing unit (packing height 150 mm) having 13.37 kg on a dry basis of the aforementioned immobilized lipase packed in a column made of stainless steel (inner diameter 600 mm, height 1050 mm) equipped with a jacket, was stacked in four stages, with each packing unit being spaced apart (height 150 mm), and the rate of liquid supply was set at 5655 mL/min. The results are presented in Table 2.

Example 7

A hydrolysis reaction was performed in the same procedure as in Example 1, except that a packed bed (packing height 150 mm) having 13.37 kg on a dry basis of the aforementioned immobilized lipase packed in a column made of stainless steel (inner diameter 600 mm, height 2250 mm) equipped with a jacket, was stacked in eight stages, with each packing unit being spaced apart (height 150 mm), and the rate of liquid supply was set at 5655 mL/min. The results are presented in Table 2.

Example 8

A hydrolysis reaction was performed in the same procedure as in Example 1, except that a packing unit (packing height 75 mm) having 0.085 kg on a dry basis of the aforementioned immobilized lipase packed in a column made of stainless steel (inner diameter 70 mm, height 1125 mm) equipped with a jacket, was stacked in eight stages, with each packing unit being spaced apart (height 75 mm). The results are presented in Table 2.

Example 9

A hydrolysis reaction was performed in the same procedure as in Example 1, except that a packing unit (packing height 150 mm) having 0.1725 kg on a dry basis of the aforementioned immobilized lipase packed in a column made of stainless steel (inner diameter 70 mm, height 645 mm) equipped with a jacket, was stacked in four stages, with each packing unit being spaced apart (height 15 mm). The results are presented in Table 2.

TABLE 1

|  |  | Reference Example 1 | Reference Example 2 | Example 1 | Example 2 | Example 3 | Example 4 |
|---|---|---|---|---|---|---|---|
| Column diameter | mm | 10 | 10 | 70 | 70 | 76.4 | 70 |
| Thickness of enzyme packing unit | mm | 1200 | 200 | 150 | 150 | 170 | 150 |
| Thickness of space | mm | 0 | 150 | 0 | 0 | 0 | 150 |
| Number of stages in packing unit | stage | 1 | 6 | 1 | 1 | 1 | 4 |
| Number of passages | Number of times | 1 | 1 | 1 | 4 | 8 | 1 |
| Total thickness of packing units |  | 1200 | 1200 | 150 | 600 | 1360 | 600 |
| Multistage/stepwise mixing |  |  | Multistage |  | Stepwise mixing | Stepwise mixing | Multistage |
| Liquid supply flow rate | mL/min. | 1.57 | 1.57 | 77 | 77 | 92 | 77 |
| Amount of packed enzyme | kg-dry | 0.027 | 0.029 | 0.16 | 0.713 | 1.68 | 0.712 |
| Porosity |  | 0.541 | 0.511 | 0.552 | 0.501 | 0.564 | 0.502 |
| Retention time in packing unit | min. | 32.438 | 30.661 | 4.142 | 15.031 | 38.319 | 15.056 |
| Acid value |  | 169.4 | 171.1 | 82 | 157 | 169.1 | 157.2 |
| Rate of degradation | (%) | 84.7 | 85.6 | 41 | 78.5 | 84.6 | 78.6 |

TABLE 1-continued

|  |  | Reference Example 1 | Reference Example 2 | Example 1 | Example 2 | Example 3 | Example 4 |
|---|---|---|---|---|---|---|---|
| Apparent activity of immobilized enzyme | U/g | 791.7 | 807.7 | 744.6 | 838 | 724.8 | 875 |

TABLE 2

|  |  | Example 5 | Example 6 | Example 7 | Example 8 | Example 9 |
|---|---|---|---|---|---|---|
| Column diameter | mm | 600 | 600 | 600 | 70 | 70 |
| Thickness of enzyme packing unit | mm | 150 | 150 | 150 | 75 | 150 |
| Thickness of space | mm | 0 | 150 | 150 | 75 | 15 |
| Number of stages in packing unit | Stage | 1 | 4 | 8 | 8 | 4 |
| Number of passages | Number of times | 1 | 1 | 1 | 1 | 1 |
| Total thickness of packing units |  | 150 | 600 | 1200 | 600 | 600 |
| Multistage/stepwise mixing |  |  | Multistage | Multistage | Multistage | Multistage |
| Liquid supply flow rate | mL/min. | 5655 | 5655 | 5655 | 77 | 77 |
| Amount of packed enzyme | kg-dry | 13.37 | 53.48 | 106.96 | 0.68 | 0.69 |
| Porosity |  | 0.491 | 0.491 | 0.491 | 0.524 | 0.517 |
| Retention time in packing unit | min. | 3.681 | 14.723 | 29.445 | 15.727 | 15.518 |
| Acid value |  | 90.7 | 154 | 170.9 | 160.3 | 160.4 |
| Rate of degradation | (%) | 45.4 | 77.0 | 85.5 | 80.2 | 80.2 |
| Apparent activity of immobilized enzyme | U/g | 767.9 | 767.9 | 767.9 | 1041.488 | 1017.781 |

Comparative Example 1

A hydrolysis reaction was performed in the same procedure as in Example 1, except that 0.36 kg on a dry basis of the aforementioned immobilized lipase was packed (packing height 300 mm) in a column made of stainless steel (inner diameter 70 mm, height 300 mm) equipped with a jacket. The results are presented in Table 3.

Comparative Example 2

A hydrolysis reaction was performed in the same procedure as in Example 1, except that 0.35 kg on a dry basis of the aforementioned immobilized lipase was packed (packing height 300 mm) in a column made of stainless steel (inner diameter 70 mm, height 300 mm) equipped with a jacket. Subsequently, the reaction liquid which had passed through the column was first subjected to oil-water separation to fractionate the oil phase, subsequently fresh water was added and mixed, and the mixture was supplied again into another column having the same shape. The hydrolysis reaction was performed two times in total by the same procedure. The results are presented in Table 3.

Comparative Example 3

A hydrolysis reaction was performed in the same procedure as in Example 1, except that a packing unit (packing height 300 mm) having 0.35 kg on a dry basis of the aforementioned immobilized lipase packed in a column made of stainless steel (inner diameter 70 mm, height 1650 mm) equipped with a jacket, was stacked in four stages, with each packing unit being spaced apart (height 150 mm). The results are presented in Table 3.

Comparative Example 4

A hydrolysis reaction was performed in the same procedure as in Example 1, except that 1.2 kg on a dry basis of the aforementioned immobilized lipase was packed (packing height 1177 mm) in a column made of stainless steel (inner diameter 70 mm, height 1300 mm) equipped with a jacket. The results are presented in Table 3.

Comparative Example 5

A hydrolysis reaction was performed in the same procedure as in Example 1, except that 103.0 kg on a dry basis of the aforementioned immobilized lipase was packed (packing height 1300 mm) in a column made of stainless steel (inner diameter 600 mm, height 1500 mm) equipped with a jacket, and the rate of liquid supply was set at 5655 mL/min. The results are presented in Table 3.

TABLE 3

|  |  | Comparative Example 1 | Comparative Example 2 | Comparative Example 3 | Comparative Example 4 | Comparative Example 5 |
|---|---|---|---|---|---|---|
| Column diameter | mm | 70 | 70 | 70 | 70 | 600 |
| Thickness of enzyme packing unit | mm | 300 | 300 | 300 | 1177 | 1300 |
| Thickness of space | mm | 0 | 0 | 150 | 0 | 0 |
| Number of stages in packing unit | Stage | 1 | 1 | 4 | 1 | 1 |

TABLE 3-continued

|  |  | Comparative Example 1 | Comparative Example 2 | Comparative Example 3 | Comparative Example 4 | Comparative Example 5 |
|---|---|---|---|---|---|---|
| Number of passages | Number of times | 1 | 2 | 1 | 1 | 1 |
| Total thickness of packing unit |  | 300 | 600 | 1200 | 1177 | 1300 |
| Multistage/stepwise mixing |  |  | Stepwise mixing | Multistage |  |  |
| Liquid supply flow rate | mL/min. | 77 | 77 | 77 | 77 | 5655 |
| Amount of packed enzyme | kg-dry | 0.36 | 0.7 | 1.4 | 1.2 | 103 |
| Porosity |  | 0.496 | 0.496 | 0.496 | 0.57 | 0.547 |
| Retention time | min. | 7.444 | 14.888 | 29.776 | 33.453 | 35.574 |
| Acid value |  | 98.6 | 135.4 | 156.3 | 149.8 | 125 |
| Rate of degradation | (%) | 49.3 | 67.7 | 78.15 | 74.9 | 62.5 |
| Apparent activity of immobilized enzyme | U/g | 457.5 | 470.4 | 419.2 | 407.4 | 222.3 |

From the results shown in Table 1 to Table 3, it is clear that the (apparent) activity of the immobilized enzyme was effectively appeared by defining the packing thickness of the immobilized enzyme per stage in the fixed bed-type reaction column. Furthermore, when a multistage fixed bed-type reaction column having packing units and space alternately is used as the reaction column, the (apparent) activity of the immobilized enzyme can be more effectively appeared, and thus it is clear that the rate of hydrolysis of oils and fats is enhanced.

The invention claimed is:

1. A process for producing fatty acids, which comprises feeding a liquid mixture formed of two liquid phases comprising an oil phase substrate and an aqueous phase substrate into a multistage fixed bed-type reaction column having an equivalent circular diameter of 35 mmφ or larger and containing two or more stages of packing units packed with an immobilized lipase enzyme stacked so that each packing unit is spaced apart at a distance of from 1 to 200 mm, and allowing the liquid mixture to flow in the same direction in a co-current manner to perform a hydrolysis reaction, wherein the packing thickness of the immobilized lipase enzyme per stage of the multistage fixed bed-type reaction column is from 10 to 200 mm.

2. The process for producing fatty acids according to claim 1 wherein the packing unit is spaced apart at a distance of at least equal to or less than the thickness of the packing unit.

3. The process for producing fatty acids according to claim 1 or 2, wherein the oil phase substrate comprises plant oil, animal oil, or a mixture thereof.

4. The process for producing fatty acids according to claim 1 or 2, wherein the aqueous phase substrate comprises water.

5. The process for producing fatty acids according to claim 1, wherein each packing unit is spaced apart at a distance from 5 to 200 mm.

6. The process for producing fatty acids according to claim 1, wherein an equivalent circular diameter of the multistage fixed bed-type reaction column is 35 to 10,000 mmφ.

* * * * *